(12) United States Patent
Klein et al.

(10) Patent No.: US 8,088,105 B2
(45) Date of Patent: Jan. 3, 2012

(54) SYRINGE PUMP

(75) Inventors: Ronnie Klein, Haifa (IL); Amnon Weichselbaum, Haifa (IL)

(73) Assignee: Fertiligent Ltd., Raanana (IL)

( * ) Notice: Subject to any disclaimer, the term of this patent is extended or adjusted under 35 U.S.C. 154(b) by 577 days.

(21) Appl. No.: 12/186,616

(22) Filed: Aug. 6, 2008

(65) Prior Publication Data

US 2008/0294110 A1 Nov. 27, 2008

Related U.S. Application Data

(63) Continuation-in-part of application No. 10/810,686, filed on Mar. 29, 2004, now abandoned.

(51) Int. Cl.
*A61M 37/00* (2006.01)
*A61M 1/00* (2006.01)
(52) U.S. Cl. ........................... 604/131; 604/151
(58) Field of Classification Search .......... 604/131–155; 600/33, 35
See application file for complete search history.

(56) References Cited

U.S. PATENT DOCUMENTS

| 7,270,648 | B2 * | 9/2007 | Kazemzadeh | 604/135 |
| 7,530,968 | B2 * | 5/2009 | Gonnelli | 604/132 |
| 2002/0177805 | A1 * | 11/2002 | Barker et al. | 604/85 |

* cited by examiner

*Primary Examiner* — Matthew F Desanto
(74) *Attorney, Agent, or Firm* — Dekel Patent Ltd.; David Klein

(57) ABSTRACT

A syringe pump including a syringe including a plunger that slides in a body which has a discharge port, a driving mechanism coupled to the syringe, including a cylinder in which a piston slides, and a plurality of biasing devices arranged about the piston operative to apply urging forces on the piston to drive the piston distally in the cylinder and thereby cause the plunger to slide in the body and discharge a substance found in the body through the discharge port, wherein if one of the biasing devices fails another of the biasing devices continues to apply a force on the piston to drive the piston distally in the cylinder, and a safety catch that initially prevents the biasing device from moving the piston, the safety catch being removable to permit the biasing device to move the piston.

6 Claims, 5 Drawing Sheets

SYRINGE PUMP

CROSS REFERENCE TO OTHER APPLICATIONS

This application is a continuation-in-part of U.S. patent application Ser. No. 10/810,686, filed Mar. 29, 2004, now abandoned and claims priority therefrom.

FIELD OF THE INVENTION

The present invention relates generally to syringe pumps, and particularly to a disposable syringe pump for sperm delivery, such as in slow-release insemination.

BACKGROUND OF THE INVENTION

Microfluidic pumping devices are used in numerous applications, such as administration of medicine and biological and pharmaceutical research. Such pumping devices include mechanical pumps, such as syringe-type pumps and micromechanical pumps, and non-mechanical pumps, such as electrohydrodynamic pumps, electro-osmotic flow pumps, electrowetting pumps, and thermocapillary pumps.

There are drawbacks to different pumping devices. For example, a steady flow rate is difficult to achieve. Moreover, many mechanical pumps require an electrical power source, as do pumps that operate based on electrical properties. Many of these pumps are costly and often have slow response times.

Conventional syringe pumps are typically employed with either a syringe or a vial and plunger system for administering a liquid to a patient. In such conventional systems, a syringe or vial of the liquid is oriented vertically in a fixed position on the syringe pump. The bottom of the syringe or vial defines a discharge port connected to a flexible, hollow tubing which extends to the patient. The plunger or piston of the apparatus is engaged with the moving pusher plate or drive member of the syringe pump and is driven downwardly into the syringe body or vial to force the liquid agent from the syringe body or vial through the tubing and into the patient.

An example of such a syringe pump is described in a system of PCT published patent application WO03008102. The system employs a microchannel and a gravity driven pump comprising horizontally oriented fluid supply reservoirs. The pump supplies fluid to the microchannel at a substantially constant rate. The device may be used, among other things, for motile sperm sorting.

SUMMARY OF THE INVENTION

The present invention seeks to provide a novel, disposable syringe pump for sperm delivery, such as in slow-release insemination, as described more in detail hereinbelow. The invention may have other applications and is not limited just to slow-release insemination. For example, the invention may be used in the laboratory or other research area for pumping sperm and other fluids.

There is thus provided in accordance with an embodiment of the present invention a pump including a syringe including a plunger that slides in a body which has a discharge port, a driving mechanism coupled to the syringe, including a cylinder in which a piston slides, and a plurality of biasing devices arranged (e.g., symmetrically arranged) about the piston operative to apply urging forces on the piston to drive the piston distally in the cylinder and thereby cause the plunger to slide in the body and discharge a substance found in the body through the discharge port, wherein if one of the biasing devices fails another of the biasing devices continues to apply a force on the piston to drive the piston distally in the cylinder, and a safety catch that initially prevents the biasing device from moving the piston, the safety catch being removable to permit the biasing device to move the piston.

The safety catch may be initially held in place by a breakable element, and an actuator may be provided, which when actuated breaks the breakable element and releases the safety catch to allow the piston to start traveling in the cylinder by the force of the biasing devices.

In accordance with an embodiment of the present invention the cylinder is at least partially filled with a hydraulic fluid, and as the piston slides in the cylinder, the hydraulic fluid flows from in front of the piston to behind the piston, whereupon the hydraulic fluid continues to flow through a tube out a needle. The biasing forces of the biasing devices and hydraulic damping of the hydraulic fluid provide a close-to-linear pumping force.

The tip of the needle may be covered with a sponge, which does not interfere with flow of the hydraulic fluid therethrough and yet prevents dehydration of the hydraulic fluid when the syringe pump is in long storage.

A finishing button may be arranged to push a portion of the tube against a knife, so as to cut the tube, whereupon cutting the tube, the hydraulic fluid suddenly flows through the tube instead of the needle.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
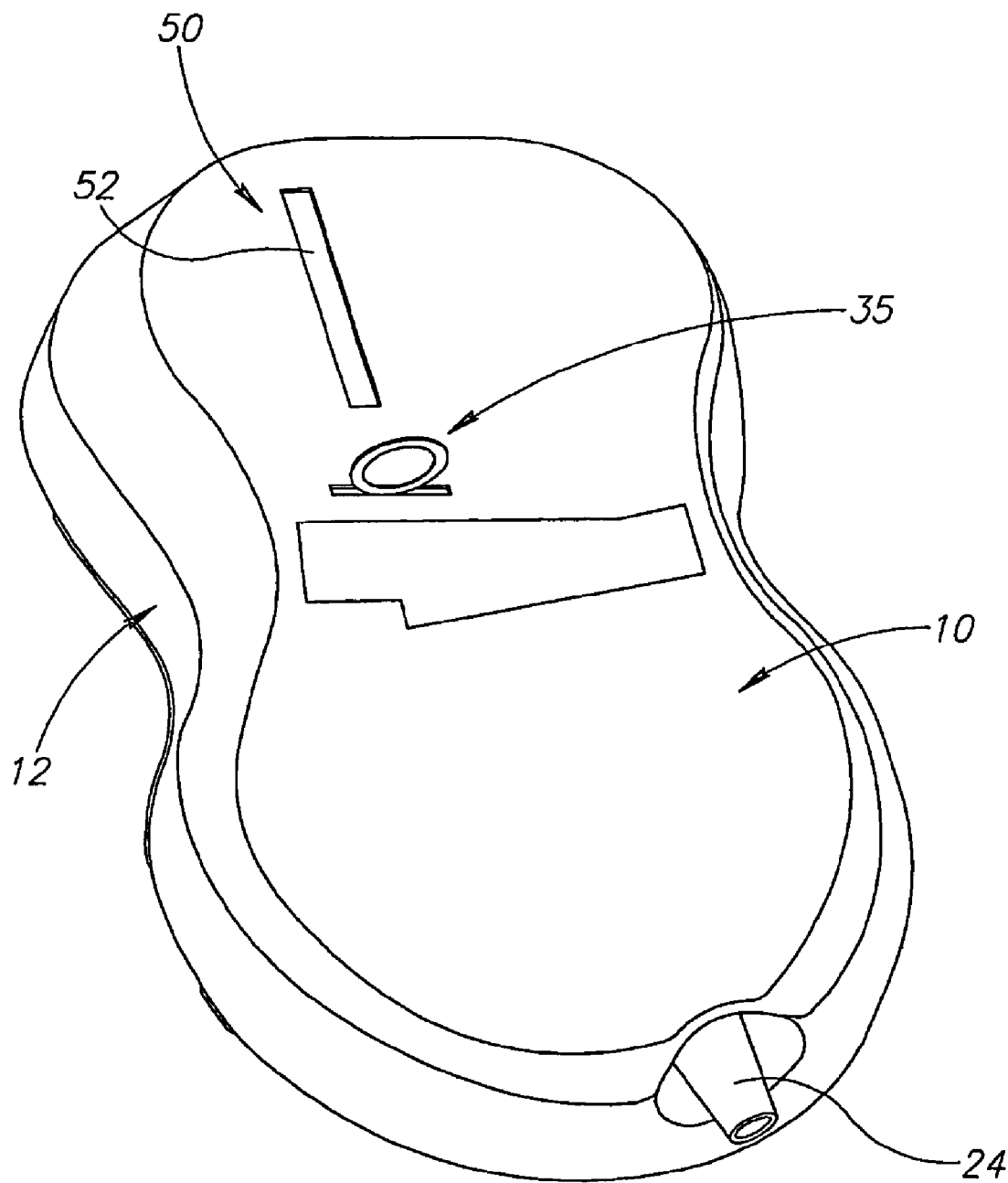
FIG. 1 is a simplified pictorial illustration of a disposable syringe pump, constructed and operative in accordance with an embodiment of the present invention.
Figure 2:
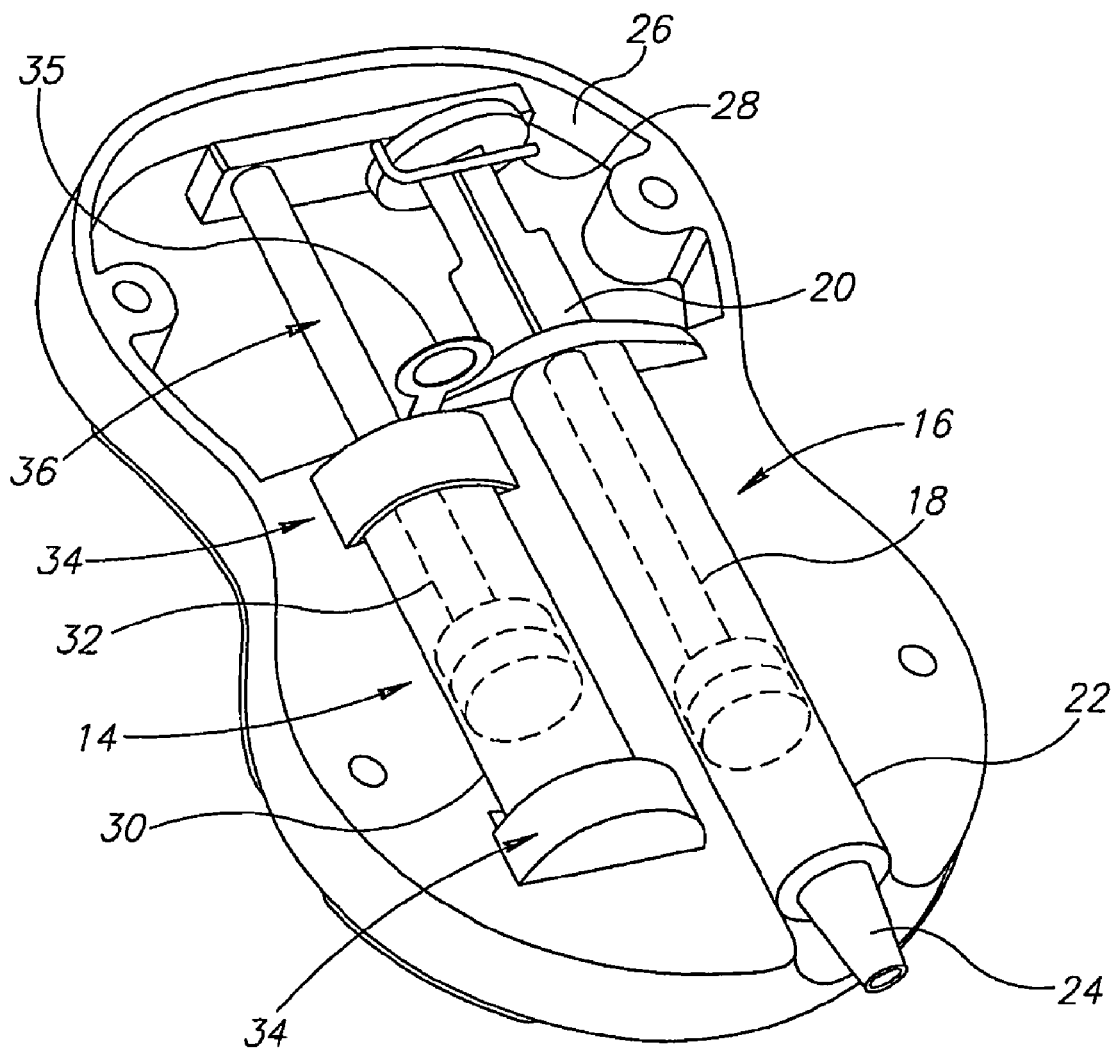
FIG. 2 is a simplified cutaway illustration of the syringe pump of FIG. 1, showing inner components thereof.

Reference is now made to FIG. 1, which illustrates a syringe pump 10, constructed and operative in accordance with an embodiment of the present invention.

The syringe pump 10 may include an outer casing 12, in which are housed a driving mechanism 14 coupled to a syringe 16. The casing 12 is illustrated as being constructed of two halves joined together (e.g., by screws, bonding, sonic welding or any other suitable method of connection), but may be constructed of one part or many parts as well. The syringe pump 10 may have any size and shape, which may depend, among other things, on the size and shape of the syringe 16 and the required flow rate. In one non-limiting embodiment of the invention, syringe pump 10 may be about 5-9 cm long, 5 cm wide and 3 cm thick.

The syringe 16 may include a body 18 in which a plunger 20 slides. The body 18 may hold any suitable volume of sperm 22, such as but not limited to, about 0.3-1.5 cc. The syringe 16 may have a discharge port 24, which may be connected to suitable tubing and a filter (not shown) for sperm delivery, such as in slow-release insemination. The syringe 16 and its parts may be made of any medically safe material, such as but not limited to, polycarbonate, and may be completely disposable.

The driving mechanism 14 may be coupled to a head 26 of plunger 20, such as by means of a clasp 28 or any other suitable link or connection. The driving mechanism 14 may include a cylinder 30 in which a piston 32 slides. The travel of piston 32 inside cylinder 30 may be bounded by end caps 34. Piston 32 may be mounted on a shaft 36, which is connected to clasp 28.

Figure 3:
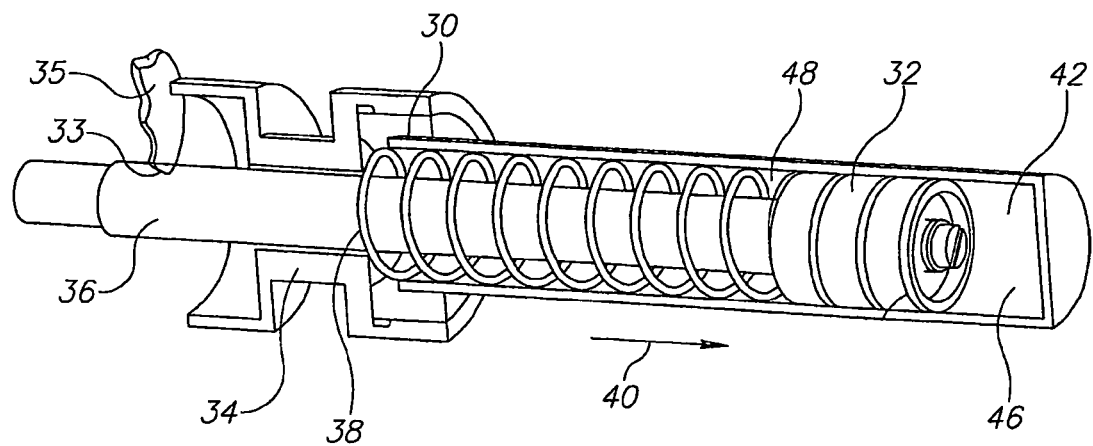
FIG. 3 is a simplified cutaway illustration of a driving mechanism used in the syringe pump of FIG. 1, constructed and operative in accordance with an embodiment of the present invention.
Figure 4:
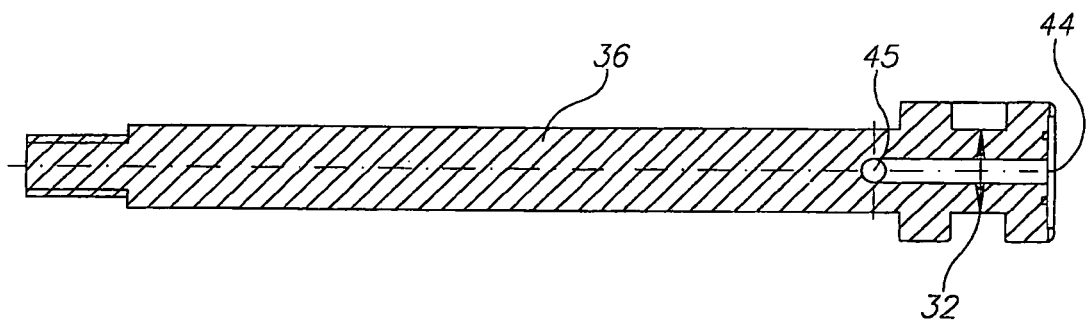
FIG. 4 is a sectional illustration of a plunger used in the driving mechanism of FIG. 3, in accordance with an embodiment of the present invention.

Reference is now made additionally to FIGS. 3 and 4. The driving mechanism 14 may include a biasing device 38, such as but not limited to, a coil spring, disposed on a portion of shaft 36 proximal to the piston 32. The biasing device 38 is operative to apply an urging force on piston 32 to drive piston 32 distally (in the direction of an arrow 40) in cylinder 30. Initially, a safety catch 35 may arrest movement of shaft 36 and piston 32. For example, the safety catch 35 may initially abut against one of the end caps 34 and sit in a notch 33 formed in shaft 36, thereby preventing biasing device 38 from expanding and moving piston 32.

Cylinder 30 may be at least partially filled with a hydraulic fluid 42, such as but not limited to, glycerin. Piston 32 may be formed with a relatively tiny vent hole 44 (such as but not limited to, a diameter of 0.1 mm) that passes through the thickness of piston 32 and is in fluid communication with a port 45 in shaft 36 on the proximal side of piston 32 (see FIG. 4). The combination of vent hole 44 and port 45 permit flow of hydraulic fluid 42 from a distal portion 46 of cylinder 30 (that is, in front of piston 32) to a proximal portion 48 of cylinder 30 (that is, behind piston 32) (see FIG. 3). Accordingly, after removal of safety catch 35, biasing device 38 pushes piston 32 distally in the direction of arrow 40, and hydraulic fluid 42 is transferred between the distal portion 46 to the proximal portion 48 of cylinder 30 (located at the posterior end of the moving plunger) via vent hole 44 and port 45. The combination of the biasing force of biasing device 38 and the hydraulic damping of the hydraulic fluid 42 may provide a close-to-linear pumping force.

As seen in FIG. 3, a regulator valve 49 may be disposed in the vent hole 44 that regulates the transfer of hydraulic fluid 42 between the distal portion 46 to the proximal portion 48 of cylinder 30. The regulator valve 49 may include a threaded screw shaft that may be turned (e.g., with a screwdriver) to regulate the size of the opening for passage therethrough of hydraulic fluid 42.

Referring again to FIG. 1, it is seen that the casing 12 may be provided with a window 50 through which the travel and forward progress of driving mechanism 14 may be observed. For example, the widow 50 may expose a tab 52 formed on shaft 36, which easily allows observation of the movement of shaft 36.

The flow or pumping rate of syringe pump 10 may be adjusted by adjusting or selecting different operating parameters, such as but not limited to, the spring coefficient of biasing device 38, sizes and shapes of vent hole 44 and port 45, the position of regulator valve 49, the cross sectional area of cylinder 30 and of body 18, and/or the viscosity of hydraulic fluid 42 (e.g., in the range of 50-1000 centipoise at 20° C.).

Figure 5A:
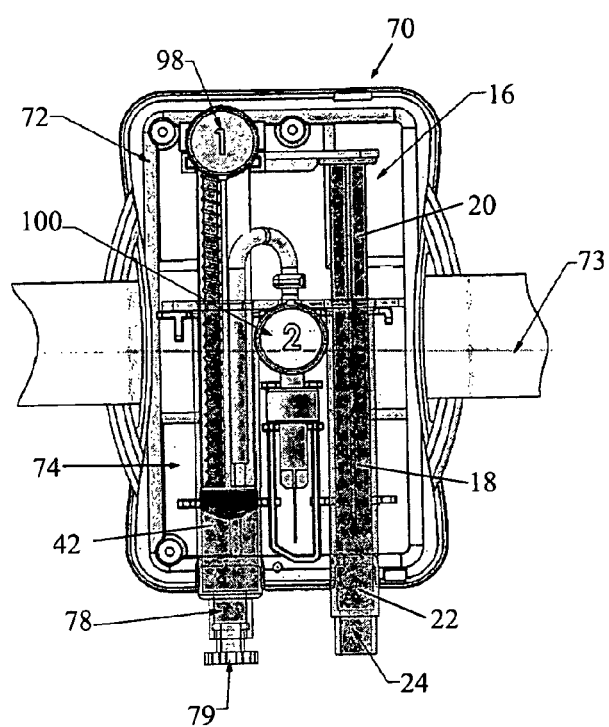
FIGS. 5A and 5B are simplified plan view and perspective view illustrations, respectively, of a disposable syringe pump, constructed and operative in accordance with another embodiment of the present invention.
Figure 5B:
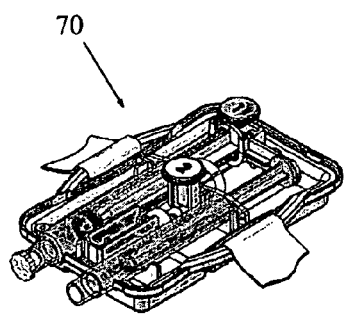

Reference is now made to FIGS. 5A and 5B, which illustrate a disposable syringe pump 70, constructed and operative in accordance with another embodiment of the present invention.

As in the previous embodiment, the syringe pump 70 may include an outer casing 72, in which are housed a driving mechanism 74 coupled to syringe 16. As before, syringe 16 includes body 18 in which plunger 20 slides, and body 18 may hold any suitable volume of sperm 22 for discharging through discharge port 24. Outer casing 72 may be provided with a strap 73 for attaching to a person or some object.

Figure 7B:
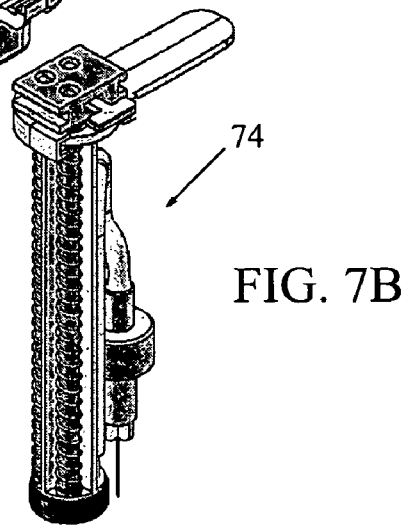
FIGS. 7A and 7B are two simplified perspective view illustrations of a driving mechanism of the syringe pump of FIGS. 5A and 5B, constructed and operative in accordance with another embodiment of the present invention.
Figure 7A:
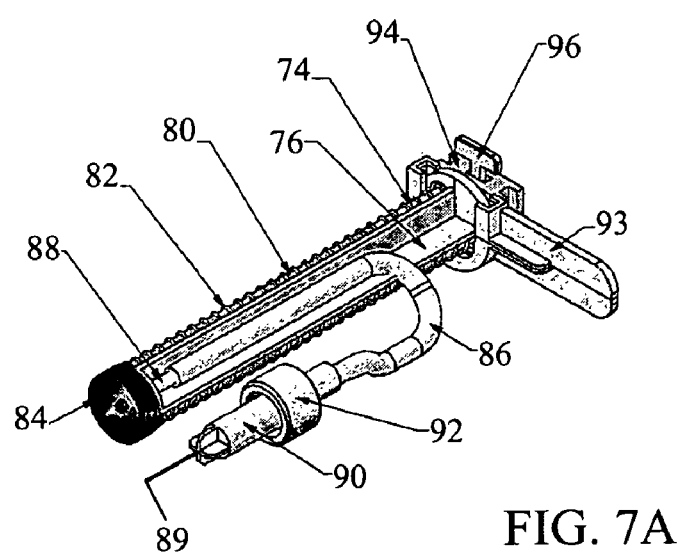

Reference is now made to FIGS. 7A and 7B. Driving mechanism 74 includes a piston 76 (also called plunger or plunger rod) which slides in a syringe cylinder 78 which is sealed by a cap 79 (seen in FIG. 5A). Driving mechanism 74 includes a plurality of biasing devices 80, such as but not limited to, three coil springs symmetrically arranged about piston 76 (i.e., 120° apart). The coil springs are mounted on spring guides 82. Piston 76 is capped by a sealing cap 84 at a distal end thereof. A tube 86 is fluidly connected to a vent tube 88 at the distal end of piston 76. The other end of tube 86 is connected to a needle 90 via a male Luer lock 92. A lever arm 93 is mounted on the proximal end of piston 76 for pushing plunger 20 of syringe 16.

A safety catch 94 is mounted on the proximal end of piston 76. Safety catch 94 is initially held in place by a breakable element 96. An actuator, herein referred to as push button 98, (FIG. 5A) is provided, which when actuated (pushed) breaks breakable element 96 and thereby releases safety catch 94 to allow piston 76 to start traveling in syringe cylinder 78 by the force of biasing devices 80. The movement of piston 76 (via lever arm 93) causes plunger 20 to move in syringe 16 and discharge sperm therefrom. It is noted that push button 98 is designed in such a way that it can not be activated unintentionally. The shape of push button 98 is flat and it has to be intentionally pressed in order to activate it.

As with the previous embodiment, cylinder 78 may be at least partially filled with a hydraulic fluid 42, such as but not limited to, glycerin gel. Piston 76 may be formed with a relatively tiny vent hole as above that passes through the thickness of piston 76 to vent tube 88. As piston 76 slides in cylinder 78, hydraulic fluid 42 flows from the distal portion of cylinder 78 (that is, in front of piston 76) to the proximal portion of cylinder 78 (that is, behind piston 76), whereupon hydraulic fluid 42 continues to flow through tube 86 out needle 90. Accordingly, after removal of safety catch 94, the biasing devices 80 push piston 76 distally in cylinder 78. The combination of the biasing force of biasing devices 80 and the hydraulic damping of the hydraulic fluid 42 may provide a close-to-linear pumping force.

The tip of needle 90 may be covered with a sponge, such as a polymer (closed cell polyurethane) sponge 89, which does not interfere with the flow of hydraulic fluid 42 therethrough and yet prevents dehydration of hydraulic fluid 42 when syringe pump 70 is in long storage.

It is noted that in this embodiment, more than one biasing device is used and the biasing devices are arranged about the piston. The significance of this is twofold. First, since there is more than one biasing device, even if one of them fails the other biasing device(s) continues to apply a force on the piston to drive the piston distally in the cylinder and thus ensures proper operation of the pump. Second, the positioning of the biasing devices inside the plunger rod (piston) ensures that the biasing force is directly applied on the plunger rod and not on lever arm 93, thus avoiding deformation and seizing of the driving mechanism.

Syringe pump 70 is provided with a finishing button 100 (FIG. 5A), which can be used to change the pump activity from continuous mode to an immediate bolus activity, as is now explained.

Figure 6:
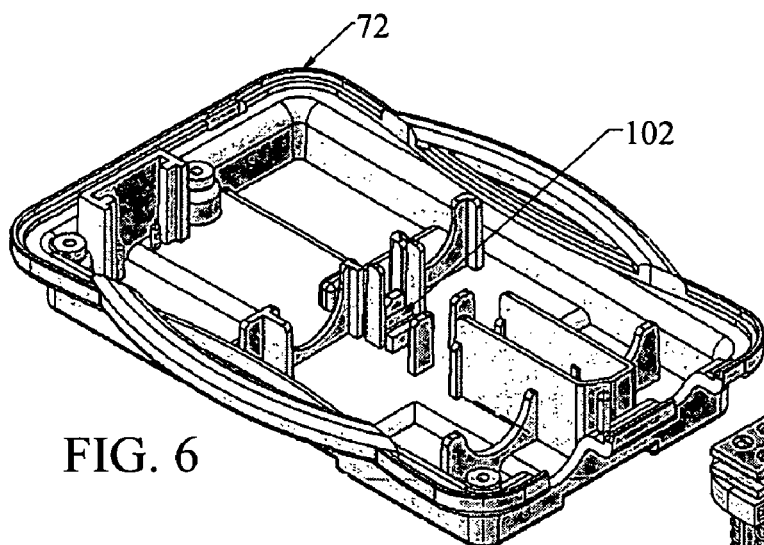
FIG. 6 is a simplified cutaway illustration of an outer casing of the syringe pump of FIGS. 5A and 5B.

Finishing button 100 is arranged to push a portion of tube 86 against a knife 102 (FIG. 6). Pressing button 100 pushes tube 86 (which may be made, without limitation, from silicone or other cuttable material) against knife 102 which cuts tube 86. Prior to cutting tube 86, hydraulic fluid 42 was forced to flow out the very small tip of needle 90. By cutting tube 86, hydraulic fluid 42 suddenly can flow through a much larger area, that is, through the diameter of severed tube 86. Thus, hydraulic fluid 42 suddenly flows through a larger diameter orifice, meaning the flow is much faster and biasing devices 80 push plunger 76 towards its distal end very quickly.

There are applications where there is a need to finish each pump cycle with a bolus shot to make sure that there is no sperm left in the syringe and catheter which is connected to the sperm container. Finishing button 100 may be used to make this bolus shot by rapidly ejecting the remaining sperm.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A syringe pump comprising:
  a syringe comprising a plunger that slides in a body which has a discharge port;
  a driving mechanism coupled to said syringe, comprising a cylinder in which a piston slides, and a plurality of biasing devices arranged about said piston operative to apply urging forces on said piston to drive said piston distally in said cylinder and thereby cause said plunger to slide in said body and discharge a substance found in said body through said discharge port, wherein if one of said biasing devices fails another of said biasing devices continues to apply a force on said piston to drive said piston distally in said cylinder; and
  a safety catch that initially prevents said biasing device from moving said piston, said safety catch being removable to permit said biasing device to move said piston, wherein said cylinder is at least partially filled with a hydraulic fluid, and as said piston slides in said cylinder, said hydraulic fluid flows from in front of said piston to behind said piston, whereupon said hydraulic fluid continues to flow through a tube out a needle.

2. The syringe pump according to claim 1, wherein said biasing devices are symmetrically arranged about said piston.

3. The syringe pump according to claim 1, wherein said safety catch is initially held in place by a breakable element, and an actuator is provided, which when actuated breaks said breakable element and releases said safety catch to allow said piston to start traveling in said cylinder by the force of said biasing devices.

4. The syringe pump according to claim 1, wherein biasing forces of said biasing devices and hydraulic damping of said hydraulic fluid provide a close-to-linear pumping force.

5. The syringe pump according to claim 1, wherein a tip of said needle is covered with a sponge, which does not interfere with flow of said hydraulic fluid therethrough and yet prevents dehydration of said hydraulic fluid when said syringe pump is in long storage.

6. The syringe pump according to claim 1, further comprising a finishing button arranged to push a portion of said tube against a knife, so as to cut said tube, whereupon cutting said tube, said hydraulic fluid suddenly flows through said tube instead of said needle.

* * * * *